United States Patent
Noda (10) Patent No.: US 9,737,275 B2
(45) Date of Patent: Aug. 22, 2017

(54) X-RAY DIAGNOSTIC APPARATUS (71) Applicant: Toshiba Medical Systems Corporation, Otawara-shi (JP)

(72) Inventor: Kouji Noda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/845,366

(22) Filed: Sep. 4, 2015

(65) Prior Publication Data

US 2016/0015345 A1    Jan. 21, 2016

Related U.S. Application Data (63) Continuation of application No. PCT/JP2014/056692, filed on Mar. 13, 2014.

(30) Foreign Application Priority Data

Mar. 14, 2013 (JP) .................................. 2013-052181

(51) Int. Cl.
*A61B 6/00* (2006.01)
*A61B 6/04* (2006.01)
(Continued)

(52) U.S. Cl.
CPC .......... *A61B 6/4441* (2013.01); *A61B 6/0407* (2013.01); *A61B 6/4464* (2013.01);
(Continued)

(58) Field of Classification Search
CPC .................................................. A61B 6/4441
See application file for complete search history.

(56) References Cited

U.S. PATENT DOCUMENTS

| 6,104,780 A | 8/2000 | Hanover et al. |
| 6,338,573 B1 * | 1/2002 | Michioka .............. F16C 19/362 104/106 |
| 6,428,206 B1 | 8/2002 | Watanabe |
| 6,461,039 B1 * | 10/2002 | Klotz ................... A61B 6/4441 378/196 |
| 7,168,855 B2 | 1/2007 | Engstrom et al. |
| 7,577,237 B2 * | 8/2009 | Zaiki ....................... A61B 6/04 378/150 |
| 2008/0101546 A1 * | 5/2008 | Delmas ................ A61B 6/4464 378/197 |

(Continued)

FOREIGN PATENT DOCUMENTS

| JP | 8-168480 A | 7/1996 |
| JP | 2000-157527 A | 6/2000 |

(Continued)

OTHER PUBLICATIONS

Notification of Transmittal of Translation of the International Preliminary Report on Patentability and Written Opinion issued on Sep. 24, 2015 in PCT/JP2014/056692.

(Continued)

*Primary Examiner* — Dani Fox
(74) *Attorney, Agent, or Firm* — Oblon, McClelland, Maier & Neustadt, L.L.P.

(57) ABSTRACT

According to one embodiment, an X-ray diagnostic apparatus includes a first arm, a second arm, a holding structure, an X-ray tube and an X-ray detector. The first arm rotates by a first rotating shaft and slides along a first arc-like slide axis relatively to the first rotating shaft. The second arm rotates by a second rotating shaft and slides along a second arc-like slide axis relatively to the second rotating shaft. The holding structure is connected with a first arm side and configured to hold the second arm. The X-ray tube and the X-ray detector are installed on the second arm.

12 Claims, 6 Drawing Sheets

(51) Int. Cl.
*F16C 19/50* (2006.01)
*F16C 29/06* (2006.01)

(52) U.S. Cl.
CPC .......... *A61B 6/4476* (2013.01); *A61B 6/4482* (2013.01); *A61B 6/501* (2013.01); *A61B 6/504* (2013.01); *A61B 6/5235* (2013.01); *A61B 6/0457* (2013.01); *A61B 6/4447* (2013.01); *A61B 6/481* (2013.01); *F16C 19/502* (2013.01); *F16C 29/0647* (2013.01)

(56) References Cited

U.S. PATENT DOCUMENTS

2011/0170668 A1* 7/2011 Ozawa .................. A61B 6/102
378/98.5

FOREIGN PATENT DOCUMENTS

| | | |
|---|---|---|
| JP | 2000-232975 A | 8/2000 |
| JP | 2001-137222 A | 5/2001 |
| JP | 2008-148925 A | 7/2008 |
| JP | 4398528 B | 10/2009 |
| JP | 2011-000376 A | 1/2011 |
| JP | 2001-145615 A | 5/2011 |

OTHER PUBLICATIONS

International Search Report issued Apr. 22, 2014 for PCT/JP2014/056692 filed on Mar. 13, 2014 with English Translation.
Written Opinion issued Apr. 22, 2014 for PCT/JP2014/056692 filed on Mar. 13, 2014.

\* cited by examiner

⇩ LOW SPEED MODE

FIG. 6B

⇩ HIGH SPEED MODE

FIG. 6C

X-RAY DIAGNOSTIC APPARATUS

CROSS REFERENCES TO RELATED APPLICATIONS

This is a continuation of Application PCT/JP2014/56692, filed on Mar. 13, 2014.

This application is based upon and claims the benefit of priority from Japanese Patent Application No. 2013-052181 filed on Mar. 14, 2013; the entire contents of which are incorporated herein by reference.

FIELD

Embodiments described herein relate generally to an X-ray diagnostic apparatus.

BACKGROUND

In an X-ray diagnostic apparatus, an X-ray generating part and an X-ray detector facing each other are held by a C-shaped arm, for example. In particular, an X-ray diagnostic apparatus that drives a pair of an X-ray generating part and an X-ray detector using multiple arms has been proposed.

As one example, an X-ray diagnostic apparatus having a structure to arrange the first slidable arc arm, overlapped with the second slidable arc arm, on a support base which is rotatable around the first rotating axis by the first rotating shaft and to attach an end part of the third arc arm, holding an X-ray generating part and an X-ray detector, in the X-ray detector side, to the second rotating shaft included in the second arc arm, has been proposed.

In the X-ray diagnostic apparatus having this structure, the X-ray generating part and the X-ray detector can be positioned by the two rotating shafts, which consist of not only the first rotating shaft, fixed on the support base, in the horizontal or vertical direction but also the second rotating shaft parallel to the X-ray exposure direction. Moreover, the X-ray generating part and the X-ray detector can also be positioned by the respective slide operations of the first arc arm and the second arc arm.

As another example, an X-ray diagnostic apparatus, which has a structure to suspend the first arc arm on a ceiling so as to rotate around the first rotating axis by the first rotating shaft, to have the second rotating shaft at one end of the first arc arm sliding along an arc track, and to attach a nearly middle part of the second arc arm, which holds an X-ray generating part and an X-ray detector at its both ends, to the second rotating shaft, has been proposed. In the X-ray diagnostic apparatus having this structure, the X-ray generating part and the X-ray detector can be positioned by the first rotating shaft fixed on the ceiling, the slide operation of the first arc arm, and the second rotating shaft.

PRIOR TECHNICAL LITERATURE

[Patent literature 1] JPA 2000-232975
[Patent literature 2] JPA 2001-145615

In the X-ray diagnostic apparatus, it is desired to enable imaging from various directions, such as a 3D (three dimensional) imaging, an imaging of an obliquely travelling blood vessel, or the like.

Accordingly, an object of the present invention is to provide an X-ray diagnostic apparatus which can easily perform various kinds of imaging, such as 3D imaging, imaging of an obliquely travelling blood vessel, or the like.

DETAILED DESCRIPTION

In general, according to one embodiment, an X-ray diagnostic apparatus includes a first arm, a second arm, a holding structure, an X-ray tube and an X-ray detector. The first arm rotates by a first rotating shaft and slides along a first arc-like slide axis relatively to the first rotating shaft. The second arm rotates by a second rotating shaft and slides along a second arc-like slide axis relatively to the second rotating shaft. The holding structure is connected with a first arm side and configured to hold the second arm. The X-ray tube and the X-ray detector are installed on the second arm.

Further, according to one embodiment, an X-ray diagnostic apparatus includes at least one arm, a rotating shaft, an X-ray tube and an X-ray detector. The at least one arm slides along an arc-like slide axis by a slide guide mechanism having a holding structure. The holding structure has balls rolling on an arc-like rail. The rotating shaft rotates the at least one arm or another arm. The X-ray tube and the X-ray detector are installed on the at least one arm, another arm rotated by the rotating shaft or further another arm.

Further, according to one embodiment, an X-ray diagnostic apparatus includes arms, an X-ray tube, an X-ray detector and a control circuit. At least one arm of the arms slides along an arc-like slide axis. The at least one arm or at least another one arm rotates around a rotation axis. The X-ray tube and the X-ray detector are installed on the at least one arm, at least another one arm rotating around the rotation axis or further another at least one arm. The control circuit is configured to control the arms. The control circuit is configured to control the arms with switching a first mode and a second mode. The arms are independently started to move and stopped in the first mode. Movements of the arms are started simultaneously at a movement start time of the X-ray tube and the X-ray detector while the arms are stopped simultaneously at a stop time of the X-ray tube and the X-ray detector in the second mode.

Further, according to one embodiment, an X-ray diagnostic apparatus includes a first arm, a holding structure and a second arm. The first arm slides along an arc-like slide axis and holds an X-ray tube and an X-ray detector. The holding structure slidably holds the first arm. The second arm is attached to at least one of a ceiling, a floor and a wall. The second arm slidably holds the holding structure.

An X-ray diagnostic apparatus according to embodiments of the present invention will be described with reference to the accompanying drawings.

Figure 1:
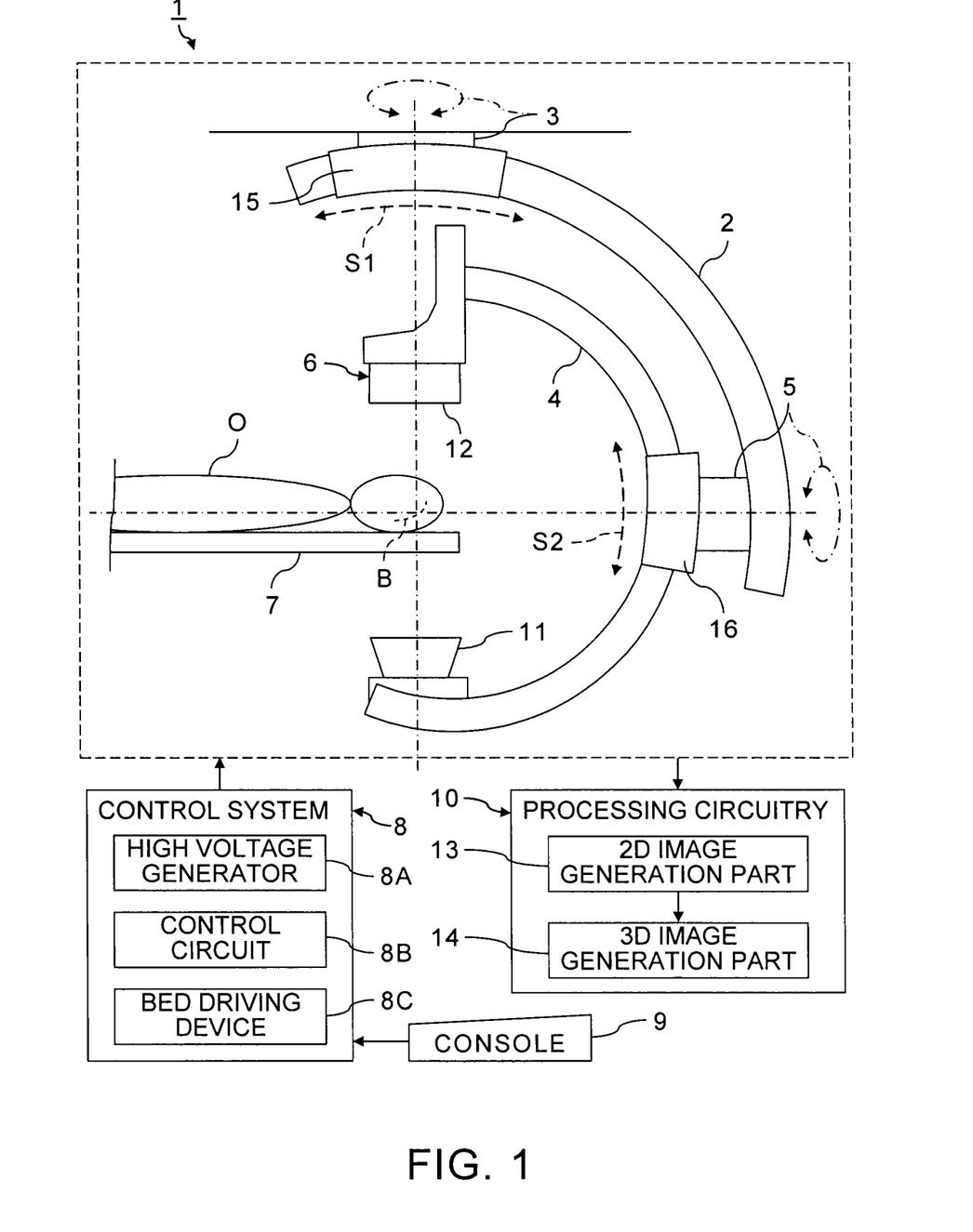
FIG. 1 is a structural view of an X-ray diagnostic apparatus according to an embodiment of the present invention.

FIG. 1 is a structural view of an X-ray diagnostic apparatus according to an embodiment of the present invention.

An X-ray diagnostic apparatus 1 includes the first arm 2, the first rotating shaft 3, the second arm 4, the second rotating shaft 5, an imaging system 6, a bed 7, a control system 8, a console 9, and processing circuitry 10. The imaging system 6 has an X-ray generating part 11 and an X-ray detector 12. The processing circuitry 10 functions as a 2D (two dimensional) image generation part 13 and a 3D image generation part 14.

The first arm 2 can be rotated around the first rotating axis by the first rotating shaft 3. The first arm 2 can be attached to a ceiling using the first rotating shaft 3 as a support post, as illustrated. Therefore, henceforth, the first arm 2 is called a support post side arm 2 while the first rotating shaft 3 is called a support post circling shaft 3.

The support post side arm 2 is configured to slide relatively to the support post circling shaft 3 along the first arc slide axis S1 by the first slide mechanism 15. Therefore, a form of the support post side arm 2 may be also arc-like. Henceforth, the first slide axis S1 is called a support post side arc slide axis S1 while the first slide mechanism 15 is called a support post side arm slide mechanism 15.

On the other hand, the second arm 4 can be rotated around the second rotating axis by the second rotating shaft 5. The imaging system 6 is attached to the second arm 4. Typically, the X-ray generating part 11, having an X-ray tube for exposing an X-ray toward an object O, is fixed to one end of the second arm 4 while the X-ray detector 12 is fixed to the other end of the second arm 4 so that the X-ray detector 12 faces to the X-ray generating part 11 across the object O set on the bed 7, as illustrated. Therefore, the second arm 4 is C-shaped. Henceforth, the second arm 4 is called a C-shaped arm 4 while the second rotating shaft 5 is called a C-shaped arm main rotating shaft 5.

The C-shaped arm 4 is configured to slide along the second arc slide axis S2, relative to the C-shaped arm main rotating shaft 5, by the second slide mechanism 16. Therefore, the second slide mechanism 16 has been connected with the support post side arm 2 side, and doubles as a holding structure for slidably holding the C-shaped arm 4. Note that, a holding structure, which is connected with the support post side arm 2 side, for holding the C-shaped arm 4 may be installed as an element different from the second slide mechanism 16.

Hereafter, the second slide axis S2 is called a C-shaped arm slide axis S2, and the second slide mechanism 16 is called a C-shaped arm slide mechanism 16. By driving the C-shaped arm 4 in the direction of the C-shaped arm slide axis S2, the C-shaped arm 4 can be rotated like a propeller, around a desired position of the C-shaped arm 4 as a rotating axis, by the C-shaped arm main rotating shaft 5. That is, the C-shaped arm main rotating shaft 5 functions as a rotating structure for rotating the C-shaped arm 4 around the second rotating axis as the center line by the second rotating shaft 5.

The C-shaped arm main rotating shaft 5 as a rotating structure for rotating the C-shaped arm 4 is fixed to the support post side arm 2. Therefore, the C-shaped arm main rotating shaft 5 itself can be moved along the support post side arc slide axis S1 with the C-shaped arm 4. In addition, the C-shaped arm 4 and the C-shaped arm main rotating shaft 5 can be rotated around the support post circling axis by the support post circling shaft 3 with the support post side arm 2. Consequently, the C-shaped arm 4 and the C-shaped arm main rotating shaft 5 can be inclined with an arbitrary angle. Note that, it is desirable that an attachment position of the C-shaped arm main rotating shaft 5 to the support post side arm 2 should be an end part of the support post side arm 2 from a viewpoint of preventing the end part of the support post side arm 2 from obstructing surrounding devices and causing interference.

Figure 2:
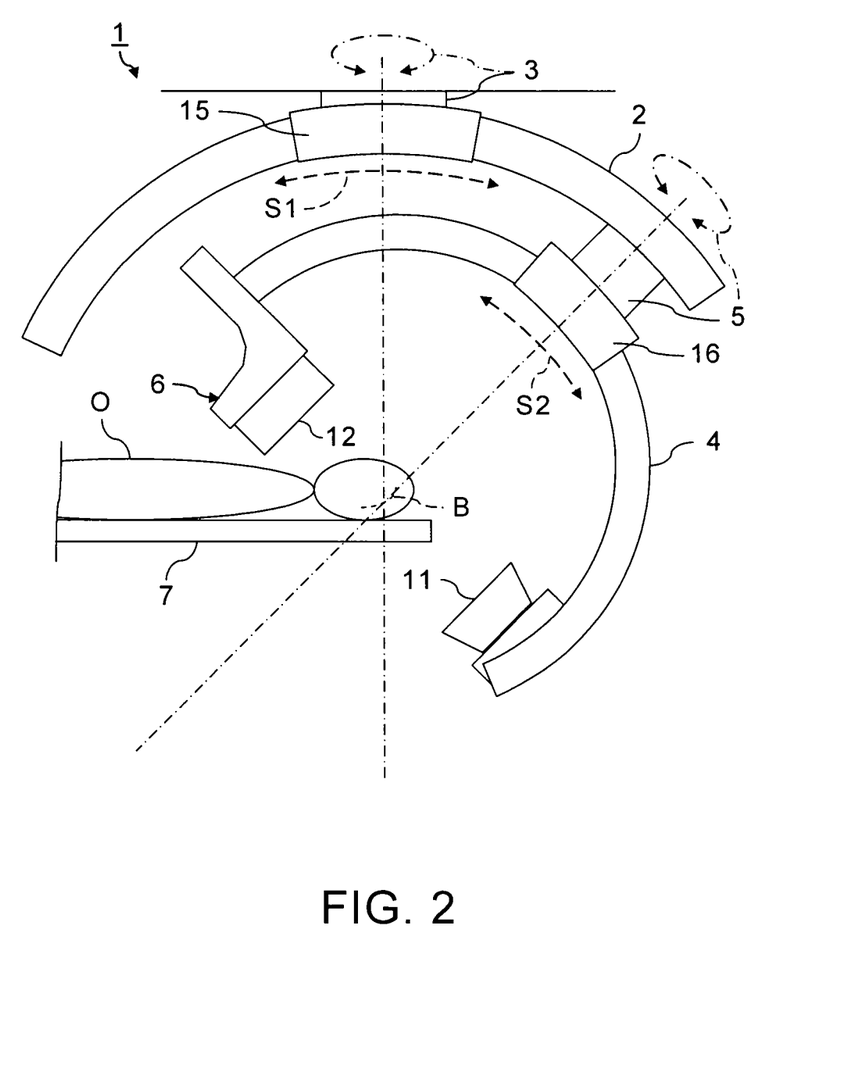
FIG. 2 is a view showing an example of inclining the C-shaped arm main rotating shaft shown in FIG. 1 according to an imaging section of an object.

FIG. 2 is a view showing an example of inclining the C-shaped arm main rotating shaft 5 shown in FIG. 1 according to an imaging section of an object O.

When the support post side arm slide mechanism 15 and the support post circling shaft 3 are operated, the C-shaped arm main rotating shaft 5 can be inclined with an arbitrary angle as shown in FIG. 2. Consequently, even when a blood vessel B which travels obliquely to the horizontal direction inside an imaging part, such as a brain or a heart, is a treatment target, the C-shaped arm main rotating shaft 5 can be positioned so as to be in parallel to the traveling direction of the obliquely travelling blood vessel B.

Then, the C-shaped arm 4 can be rotated around an isocenter (treatment center) axis like a propeller in a condition that the C-shaped arm main rotating shaft 5 has been set in the perpendicular direction to a section of the oblique travelling blood vessel B. That is, the imaging system 6 including the X-ray generating part 11 and the X-ray detector 12 can be rotated around the isocenter axis, which inclines relative to a body axis of an object O, by a rotation operation of the C-shaped arm main rotating shaft 5, so that the locus of the imaging system 6 becomes a circle. Thereby, X-ray images, on which a form of an inclining part of interest, such as an obliquely travelling blood vessel B can be observed easily, can be acquired.

Figure 3:
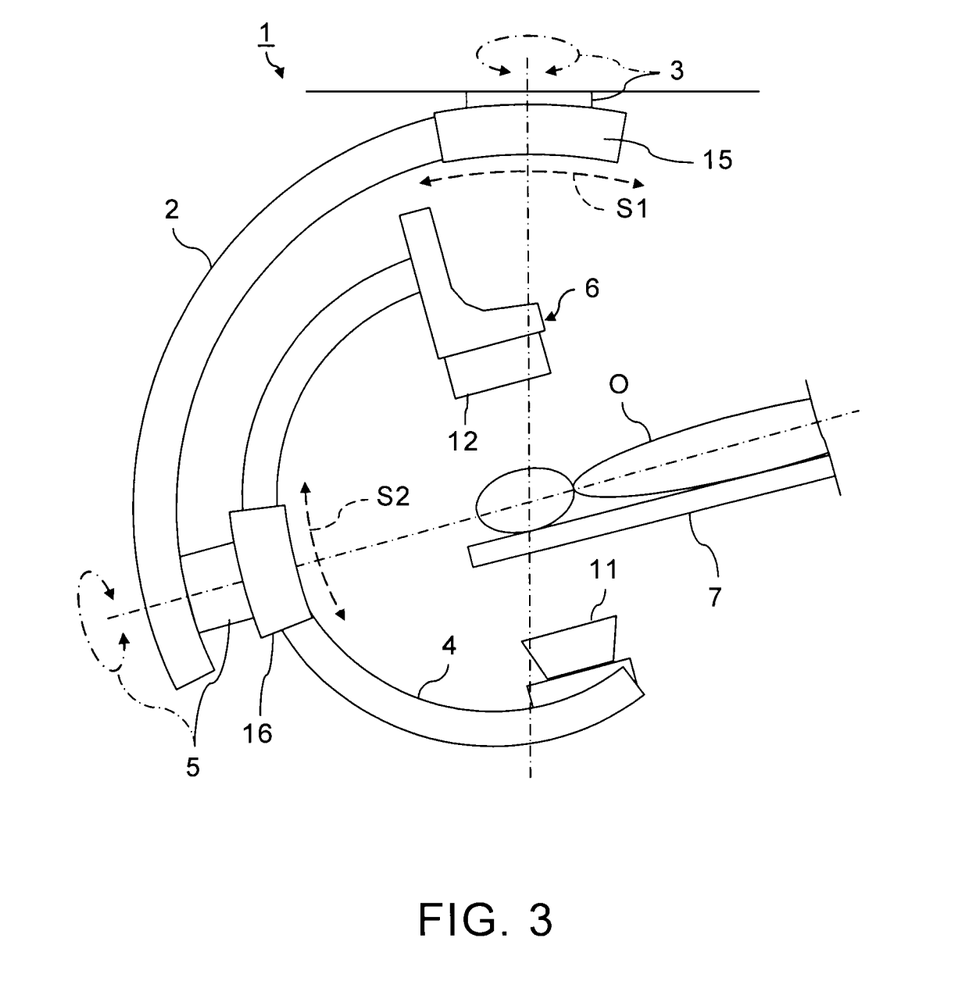
FIG. 3 shows an example of inclining the C-shaped arm main rotating shaft 5 shown in FIG. 1 according to a body axis of an object O.

FIG. 3 shows an example of inclining the C-shaped arm main rotating shaft 5 shown in FIG. 1 according to a body axis of an object O.

The C-shaped arm main rotating shaft 5 can be inclined according to not only an imaging section of an object O but also a body axis of the object O. For example, in case of using carbon dioxide as a contrast agent, it is desirable to incline the bed 7 so that an imaging part is located at a low position, since the specific gravity of carbon dioxide is heavier than that of air. In that case, the body axis of the object O inclines with the bed 7.

Thus, the C-shaped arm main rotating shaft 5 can be inclined according to the body axis of the object O, as shown in FIG. 3. On the contrary, the bed 7 for setting the object O can be inclined according to an inclined direction of the C-shaped arm main rotating shaft 5 so that carbon dioxide, which is a contrast agent, can be sufficiently supplied to an imaging part of the object O.

That is, even in a case that an imaging part of the object O is located in a lower side in height of the tilted bed 7, the C-shaped arm main rotating shaft 5 can also be inclined according to an inclined angle of the bed 7. Thus, 3D imaging can be performed with rotating the C-shaped arm 4 together with the imaging system 6 like a propeller.

As exemplified in FIG. 2 and FIG. 3, the C-shaped arm 4 can be rotated around the center axis of the C-shaped arm main rotating shaft 5, which has inclined due to a movement of the support post side arm 2.

When the support post side arc slide axis S1 and the C-shaped arm slide axis S2 are positioned on a same plane by rotation operations of the support post circling shaft 3 and the C-shaped arm main rotating shaft 5, the support post side arc slide axis S1 and the C-shaped arm slide axis S2 become concentric. Therefore, the range of the possible circling angle, on a same plane, of the C-shaped arm 4 can be a range obtained by adding a movable range of the support post side arm slide mechanism 15 to a movable range of the C-shaped arm slide mechanism 16. As a result, the imaging system 6 can be inclined over an angle range of not less than 180 degrees, for 3D imaging.

Arbitrary structures can be adopted as the support post side arm slide mechanism 15 for sliding the support post side arm 2 along the support post side arc slide axis S1 and as the C-shaped arm slide mechanism 16 for sliding the C-shaped arm 4 along the C-shaped arm slide axis S2. Typically, a slide guide mechanism in which cylindrical wheels run on arc-like curving rails can be used for one or both of the support post side arm slide mechanism 15 and the C-shaped arm slide mechanism 16.

However, the loads of the imaging system 6, the C-shaped arm 4, the C-shaped arm main rotating shaft 5, and the support post side arm 2 are born by the support post side arm slide mechanism 15. Therefore, adopting a structure having a high rigidity as the support post side arm slide mechanism 15 leads to improvement of an image quality by suppressing vibration.

Figure 4:
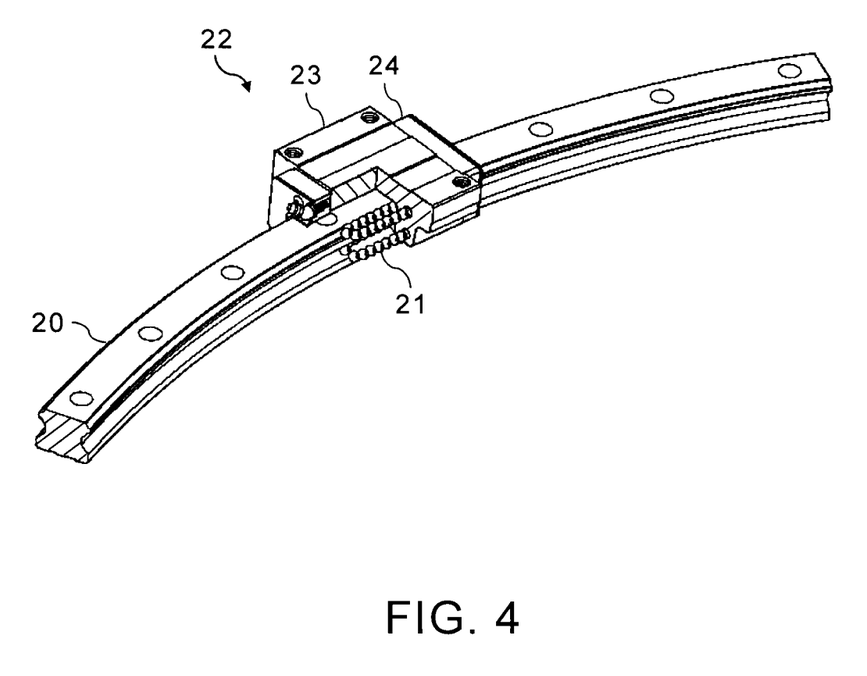
FIG. 4 is a perspective view showing an example of slide mechanism which can be adopted as the support post side arm slide mechanism and the C-shaped arm slide mechanism shown in FIG. 1.

FIG. 4 is a perspective view showing an example of slide mechanism which can be adopted as the support post side arm slide mechanism 15 and the C-shaped arm slide mechanism 16 shown in FIG. 1.

As shown in FIG. 4, a slide guide mechanism 22 having a holding structure that multiple balls 21 roll on an arc rail 20 can be used for one or both of the support post side arm slide mechanism 15 and the C-shaped arm slide mechanism 16. When at least the support post side arm 2 is configured to slide along the support post side arc slide axis S1 using the slide guide mechanism 22, which has the holding structure having the multiple rolling balls 21 as shown in FIG. 4, the loads put to the support post side arm 2 can satisfactorily be counteracted. That is, a sufficient rigidity can be attained when the slide guide mechanism 22 having the holding structure including the multiple rolling balls 21 is adopted as at least the support post side arm slide mechanism 15.

In particular, when the slide guide mechanism 22 has a holding structure that the multiple balls 21 roll on each of bearing planes formed on the four corners of the rail 20 as illustrated in FIG. 4, the equal loads can be put to the rail 20 from the four directions.

The slide guide mechanism 22 illustrated in FIG. 4 has a holding structure that a part of the multiple circulating balls 21 roll on the rail 20. Specifically, through-holes have been formed, as pathways for circulating the multiple balls 21, in a holding block 23 which slides along the rail 20. Moreover, in order to guide the balls 21 rolling from the through-holes of the holding block 23 to the pathways, of the balls 21, formed as interspaces between the bearing planes of the rail 20 and the holding block 23, end plates 24 have been prepared at the both sides of the holding block 23. Owing to such a structure of the slide guide mechanism 22, smooth slides and suppression of galling of the holding block 23 can be attained.

When the slide guide mechanism 22 as shown in FIG. 4 is also adopted to the C-shaped arm slide mechanism 16, its size can become smaller compared with the case of adopting the conventional slide mechanism having the structure in which cylindrical wheels run. Consequently, it can contribute to reduction of interference. On the contrary, the conventional slide mechanism having the structure that cylindrical wheels run may be adopted to the C-shaped arm slide mechanism 16 whose loads are relatively small. In that case, simplification of the structure and cost reduction of the C-shaped arm slide mechanism 16 can be attained.

Moreover, determination of the slide operation range of the support post side arm slide mechanism 15 allows reduction in rotary torque required for drive of the support post side arm slide mechanism 15. Specifically, by setting the slide range of the support post side arm 2 along the support post side arc slide axis S1 to be shorter than the slide range of the C-shaped arm 4 along the C-shaped arm slide axis S2, a moving speed required for operation of the support post side arm slide mechanism 15 can be slower than a moving speed of the C-shaped arm slide mechanism 16 according to the ratio of the slide operation ranges. Consequently, the reduction of the rotary torque required for drive of the support post side arm slide mechanism 15 can be attained.

Figure 5:
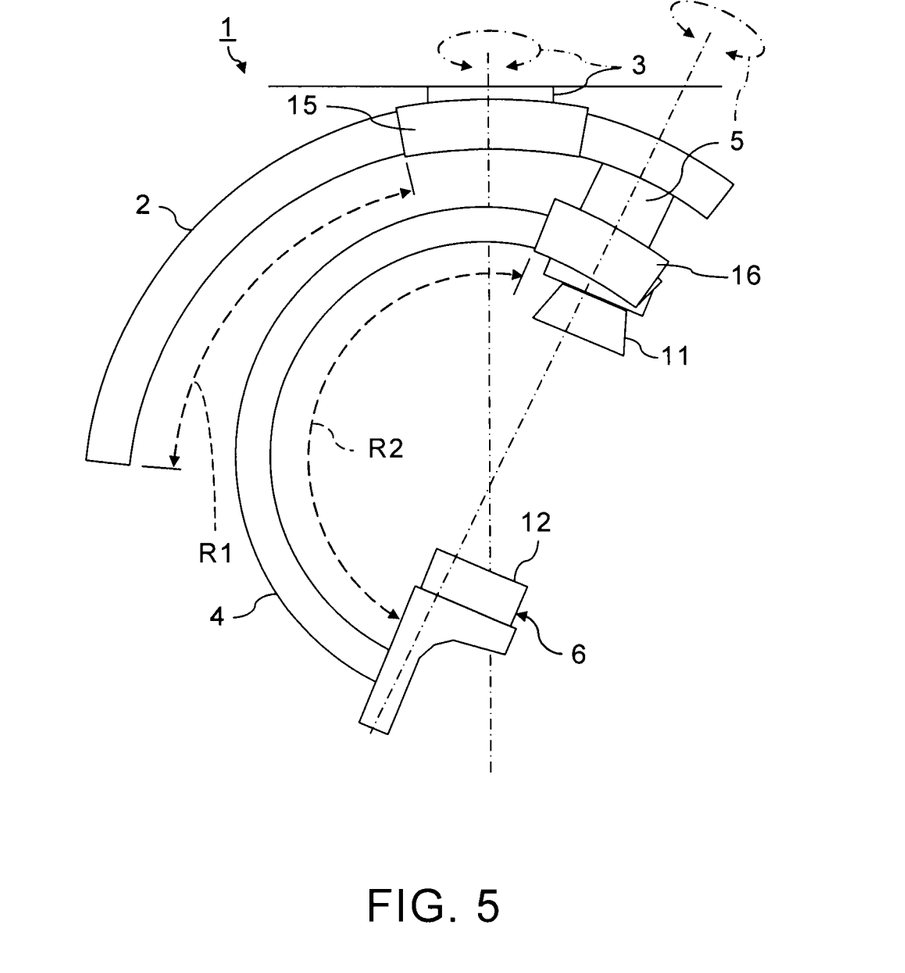
FIG. 5 is a view showing an example of the C-shaped arm rotated by slide operations by the support post side arm slide mechanism and in the C-shaped arm slide mechanism shown in FIG. 1.

FIG. 5 is a view showing an example of the C-shaped arm 4 rotated by slide operations by the support post side arm slide mechanism 15 and in the C-shaped arm slide mechanism 16 shown in FIG. 1.

As shown in FIG. 5, a rotation range of the C-shaped arm 4 in the direction of the C-shaped arm slide axis S2 can be longer than a movable range of the C-shaped arm slide mechanism 16 by the slide operations of both the support post side arm slide mechanism 15 and the C-shaped arm slide mechanism 16.

However, the loads of the imaging system 6, the C-shaped arm 4, the C-shaped arm main rotating shaft 5, and the support post side arm 2 are put to the support post side arm slide mechanism 15, as mentioned above. Therefore, the rotary torque for sliding the support post side arm 2 becomes larger than the rotary torque for sliding the C-shaped arm 4.

Accordingly, as shown in FIG. 5, a slide operation range R1 of the support post side arm 2 by the support post side arm slide mechanism 15 can be set to 40 degrees while a slide operation range R2 of the C-shaped arm 4 by the C-shaped arm slide mechanism 16 can be set to 160 degrees, for example. That is, a possible rotation angle range of the support post side arm 2 in the support post side arc slide axis S1 direction can be set to about ¼ of a possible rotation angle range of the C-shaped arm 4 in the C-shaped arm slide axis S2 direction.

Then, the moving speed of the support post side arm slide mechanism 15 becomes about ¼ of the moving speed of the C-shaped arm slide mechanism 16. Thereby, it is possible to slide the support post side arm 2, having a larger rotational torque than that of the C-shaped arm 4, using a drive power supply similar to a drive power supply for sliding the C-shaped arm 4 by the C-shaped arm slide mechanism 16.

That is, by limiting the slide operation range of the support post side arm 2 by the support post side arm slide mechanism 15, the support post side arm slide mechanism 15 can be driven using a general and practical drive power supply and drive mechanism. Note that, as an example of general drive mechanism to drive each of the C-shaped arm slide mechanism 16 and the support post side arm slide mechanism 15, a drive mechanism consisting of a servomotor and a worm speed reducer can be mentioned. Moreover, an arbitrary known drive mechanism can be used for the slide drive mechanism whether it is a slide guide mechanism by running of wheels or a slide guide mechanism by circulating and rolling of the balls 21 as shown in FIG. 4.

The control system 8 is a system having a high voltage generator 8A and a control circuit 8B for performing imaging of an object O by controlling the support post side arm 2, the C-shaped arm 4, and the imaging system 6. Specifically, the support post circling shaft 3 and the support post side arm slide mechanism 15 are controlled by control signals from the control circuit 8B. Thereby, the support post side arm 2 can be positioned. Similarly, the C-shaped arm main rotating shaft 5 and the C-shaped arm slide mechanism 16 are controlled by control signals from the control circuit 8B. Thereby, the C-shaped arm 4 can be positioned. Furthermore, an X-ray can be exposed toward an object O by applying a voltage to the X-ray generating part 11 from the high voltage generator 8A included in the control system 8. In addition, the control system 8 has other devices required for imaging, such as a bed driving device 8C which drives the bed 7. The direction information to be input into the control system 8 can be input from the console 9 having an input circuit and a display.

In particular, the control system 8 is configured to control the support post side arm 2, the C-shaped arm 4, and the imaging system 6 in the first mode and the second mode which can be mutually switched. The first mode is an independent operational mode, in which each movement of the support post side arm 2 and the C-shaped arm 4 is started and stopped by an independent slide operation. Meanwhile, the second mode is an interlocking operational mode, in which the support post side arm 2 and the C-shaped arm 4 are moved with interlocking with each other.

In the interlocking operational mode, for example, movements by slide operations of the support post side arm 2 and the C-shaped arm 4 can be started simultaneously at a movement start time of the imaging system 6 while the support post side arm 2 and the C-shaped arm 4 can be stopped simultaneously at a stop time of the imaging system 6, by controlling each moving speed of the support post side arm 2 and the C-shaped arm 4. A selection of an operational mode can be performed by inputting direction information from the console 9 into the control system 8.

The independent operational mode to independently operate each of the support post side arm 2 and the C-shaped arm 4 can be chosen mainly for imaging of an inclining imaging part as shown in FIG. 2. Meanwhile, the interlocking operational mode to operate the support post side arm 2 and the C-shaped arm 4 with interlocking can be chosen mainly in a case, such as 3D imaging, that imaging is performed by exposing X-rays towards an object O from multiple directions in an angle range of not less than 180 degrees. That is, when a movement area of the imaging system 6 by slide operations is wide, the interlocking operational mode can be chosen.

In a case that the imaging system 6 is rotated by not less than 180 degrees on the plane including the C-shaped arm main rotating shaft 5, both the C-shaped arm 4 and the support post side arm 2 slide in the plane including the C-shaped arm main rotating shaft 5, as mentioned above. It is also possible to slide both the C-shaped arm 4 and the support post side arm 2 with operating one or both of the support post circling shaft 3 and the C-shaped arm main rotating shaft 5.

Thus, in a case that both the C-shaped arm slide mechanism 16 and the support post side arm slide mechanism 15 are in operations, the moving speeds of the C-shaped arm 4 and the support post side arm 2 can be controlled so that one of the C-shaped arm 4 and the support post side arm 2 would not stop while the other is being driven, and contrarily, so that one of the C-shaped arm 4 and the support post side arm 2 would not start its drive prior to the other.

In this case, the moving speeds of the C-shaped arm 4 and the support post side arm 2 are controlled according to the slide range of the C-shaped arm 4 and the slide range of the support post side arm 2, so that the timings when the C-shaped arm 4 and the support post side arm 2 start movements from their start positions by slide operations accord to each other, and also, so that their arrival timings at stop positions accord to each other. Therefore, when a slide distance of the C-shaped arm 4 differs from a slide distance of the support post side arm 2, the movement speed of the C-shaped arm 4 is different from the movement speed of the support post side arm 2.

As a specific example, in the case that the slide range of the C-shaped arm 4 is 160 degrees and the slide range of the support post side arm 2 is 40 degrees, the movement speed of the support post side arm 2 should be set to one fourth of the movement speed of the C-shaped arm 4. For example, when the angular velocity of the C-shaped arm 4 is 40 degrees/second, the angular velocity of the support post side arm 2 should be set to 10 degrees/second.

Such a speed control allows avoiding discontinuous operations of the C-shaped arm 4 and the support post side arm 2 in all the slide operation ranges. That is, both the C-shaped arm 4 and the support post side arm 2 can be operated continuously from their moving starts to stops. Thereby, vibration due to an inertia load arising when one of the C-shaped arm 4 and the support post side arm 2 starts or stops at a timing different from that of the other can be avoided. As a result, vibration and image quality deterioration of 3D images because of the vibration can be reduced.

Figure 6A:
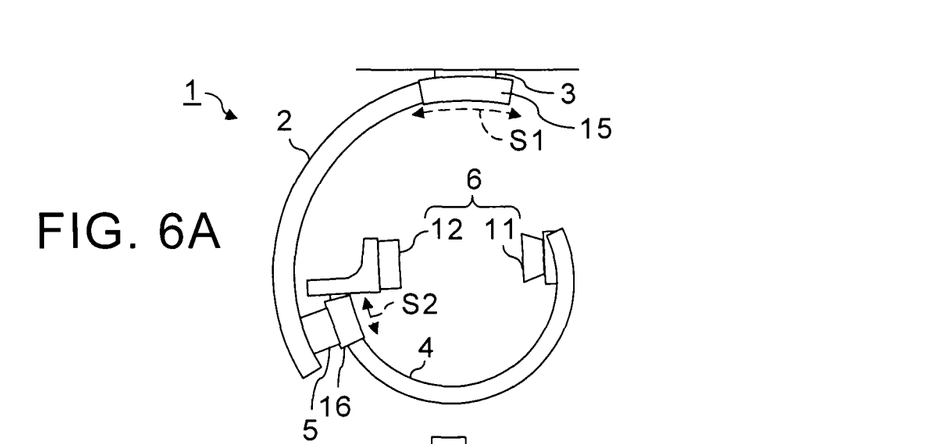
FIGS. 6A-6C show an example case of variably controlling the moving speeds of the C-shaped arm and the support post side arm shown in FIG. 1.
Figure 6B:
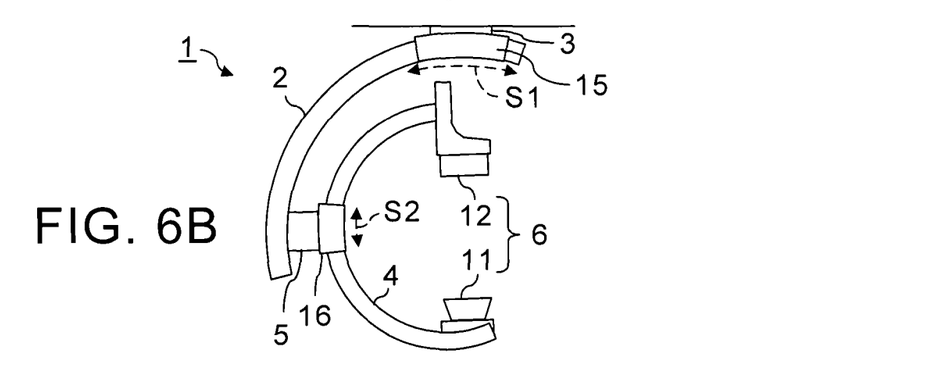
Figure 6C:
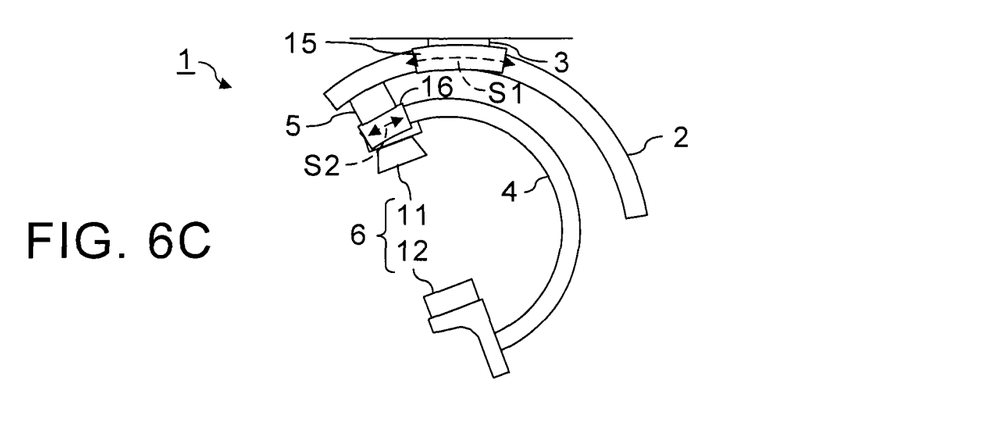

FIGS. 6A-6C show an example case of variably controlling the moving speeds of the C-shaped arm and the support post side arm shown in FIG. 1.

In the interlocking operational mode of the C-shaped arm 4 and the support post side arm 2, the moving speeds of the C-shaped arm 4 and the support post side arm 2 can also be variably controlled. Examples of an easy control include a control method that the C-shaped arm 4 and the support post side arm 2 are moved in the first moving speed mode in the first moving range until the C-shaped arm 4 and the support post side arm 2 lie predetermined positions respectively while the C-shaped arm 4 and the support post side arm 2 are moved in the second moving speed mode, which has higher speeds than those in the first moving speed mode, in the second moving range after the C-shaped arm 4 and the support post side arm 2 lie the predetermined positions respectively.

In this case, the first moving range can be a range in which suppressing vibration is important while the second moving range can be a range in which a possibility of vibration is low. Then, in the first moving range in which suppressing vibration is important, the C-shaped arm 4 and the support post side arm 2 move in the first moving speed mode, in which the moving speeds of the C-shaped arm 4 and the support post side arm 2 are comparatively slow. On the contrary, in the second moving range in which the possibility of vibration is low, the C-shaped arm 4 and the support post side arm 2 move in the second moving speed mode, in which the moving speeds of the C-shaped arm 4 and the support post side arm 2 are fast.

As a result, vibration can be suppressed since the C-shaped arm 4 and the support post side arm 2 move at a low speed in the first moving range in which suppressing vibration is important. Meanwhile, radiation exposure of the object O can be reduced since the C-shaped arm 4 and the support post side arm 2 move at a high speed in the second moving range in which the possibility of vibration is low.

The predetermined positions, which are switching positions from the first moving speed mode to the second moving speed mode, can be determined arbitrarily. For example, in a case that the C-shaped arm 4 and the support post side arm 2 located in the positional relationship shown in FIG. 6A are moved to the positions shown in FIG. 6C, the positions of the C-shaped arm 4 and the support post side arm 2 when a direction of the C-shaped arm main rotating shaft 5 becomes the horizontal direction and the X-ray exposure direction becomes the vertical direction as shown in FIG. 6B can be the predetermined positions for switching from the first moving speed mode to the second moving speed mode.

Namely, the positions of the C-shaped arm 4 and the support post side arm 2 when the direction of the C-shaped arm main rotating shaft 5 becomes the horizontal direction and the X-ray exposure direction becomes the vertical direction, as shown in FIG. 1, can be set to default positions. Then, the default positions can be set to the predetermined positions for switching from the first moving speed mode to the second moving speed mode.

In this case, the C-shaped arm 4 and the support post side arm 2 move in the low speed mode in the first moving range, in which vibration may be caused by the rotational moment applied on the support post side arm slide mechanism 15 and the support post circling shaft 3 due to own weights of the C-shaped arm 4 and the support post side arm 2, as shown in FIG. 6A. Thereby, vibration due to movements of the C-shaped arm 4 and the support post side arm 2 is suppressed.

Meanwhile, the C-shaped arm 4 and the support post side arm 2 move in the high speed mode in the second moving range, from the standard positions of the C-shaped arm 4 and the support post side arm 2 shown in FIG. 6B, to the positions as shown in FIG. 6C where the rotation moment applied on the support post side arm slide mechanism 15 and the support post circling shaft 3 becomes small. Thereby, an X-ray exposure time can be shortened and radiation exposure of the object O can be reduced.

As another example, the predetermined positions which are switching positions from the first moving speed mode to the second moving speed mode, i.e., the starting positions of the second moving range may be determined so that stop timings of the C-shaped arm 4 and the support post side arm 2 accord to each other when the C-shaped arm 4 and the support post side arm 2 move at the maximum speeds in the second moving range. In this case, the moving speeds of the C-shaped arm 4 and the support post side arm 2 in the first moving range are to be controlled so that the C-shaped arm 4 and the support post side arm 2 arrive at the predetermined positions, which are the starting positions of the second moving range, at the same timing, and also, so that the C-shaped arm 4 and the support post side arm 2 start moving from the predetermined positions at the same timing.

On the other hand, the processing circuitry 10 performs data processing of data acquired by the imaging system 6 under control of the control system 8 as described above. The 2D image generation part 13 can generate 2D X-ray image data based on X-ray detection data detected by the X-ray detector 12.

When the C-shaped arm 4 are rotated like a propeller, with inclining the C-shaped arm main rotating shaft 5 by sliding the support post side arm 2, X-ray detection data are detected by the X-ray detector 12 during a rotation of the C-shaped arm 4 around the inclined C-shaped arm main rotating shaft 5. Accordingly, the 2D image generation part 13 can generate frames of X-ray image data based on X-ray detection data detected by the X-ray detector 12 during the rotation of the C-shaped arm 4.

Furthermore, the 3D image generation part 14 can generate 3D X-ray image data, based on the frames of X-ray image data generated in the 2D image generation part 13.

That is, the X-ray diagnostic apparatus 1 as mentioned above is an apparatus which has the two arms of the C-shaped arm 4 and the support post side arm 2 for positioning the imaging system 6, and move the imaging system 6 along the four axes of the center of the support post circling shaft 3, the support post side arc slide axis S1, the center of the C-shaped arm main rotating shaft 5, and the C-shaped arm slide axis S2.

Therefore, the X-ray diagnostic apparatus 1 can be used as an apparatus for circulatory organs. In particular, according to the X-ray diagnostic apparatus 1, the C-shaped arm main rotating shaft 5 can be inclined according to a part of interest, such as an inclining blood vessel. For example, a rotation of the support post circling shaft 3 and a slide operation of the support post side arm 2 in the support post side arc slide axis S1 direction can set the C-shaped arm main rotating shaft 5 to be in parallel to a traveling direction of an arbitrary blood vessel which travels in a certain direction in a brain or a heart. Then, not only rotation imaging around a body axis of an object O but also rotation imaging around an inclining isocenter axis can be performed. Typically, rotation imaging around the direction perpendicular to a section of an inclining blood vessel can be performed. Thereby, X-ray images appropriate for understanding a form of a blood vessel can be acquired.

In addition, according to the X-ray diagnostic apparatus 1, the imaging system 6 can be moved within a large range. In particular, the imaging system 6 can be moved within a large range to cope with 3D imaging fully, using both the slide of the support post side arm 2 in the support post side arc slide axis S1 direction and the slide of the C-shaped arm 4 in the C-shaped arm slide axis S2 direction together. That is, a movement of the imaging system 6 over the slide range of the C-shaped arm 4 by the C-shaped arm slide mechanism 16 can be attained. Moreover, it is possible to perform a movement of the imaging system 6, which has been conventionally difficult, such as a slide of the C-shaped arm 4 in the C-shaped arm slide axis S2 direction in a condition that the X-ray generating part 11 and the X-ray detector 12 have been arranged at the right side and the left side of an object O. Therefore, a moving range of the imaging system 6 required for 3D imaging can fully be covered.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The embodiment mentioned above shows an example that the support post side arm 2 as the first arm 2 is attached to a ceiling through the support post circling shaft 3. However, the first arm 2 may be attached to a wall or a floor in an imaging room, for example. Specifically, the first arm 2 may be attached to a wall through the first rotating shaft 3. Alternatively, the first arm 2 may also be placed on a floor through the first rotating shaft 3.

That is, the first arm 2 can be attached to a ceiling, a wall, or a floor using the first rotating shaft 3 as a support post. In other words, an X-ray diagnostic apparatus can be configured by the second arm 4, which slides along the second arc-like slide axis S2 and holds the X-ray generating part 11 and the X-ray detector 12, a holding structure for slidably holding the second arm 4, and the first arm 2, which is attached to at least one of a ceiling, a floor and a wall and slidably holds the holding structure.

Furthermore, the respective numbers of arms, rotation axes, and slide axes may be changed. In also that case, arms of which at least one arm slides along an arc slide axis by the slide guide mechanism 22 having the holding structure that the multiple balls 21 roll on the arc rail 20 as illustrated in FIG. 4 can be installed in an X-ray diagnostic apparatus. In this case, an arm slid by the slide guide mechanisms 22 or another arm can be rotated by at least one rotation shaft. Moreover, the imaging system 6 including the X-ray generating part 11 and the X-ray detector 12 can also be attached to an arm slid by the slide guide mechanism 22 or another arm. Furthermore, multiple imaging systems 6 may also be attached to corresponding arms. In this case, the X-ray diagnostic apparatus 1 becomes a biplane type.

Note that, when each of the first arm 2 and the second arm 4 is configured to slide as the embodiments mentioned above, an interference region by the first arm 2 and the second arm 4 can be reduced. That is, it is avoidable that extremely protruding parts arise.

Moreover, the controls by the interlocking operational mode and the independent operational mode can be designated also in an X-ray diagnostic apparatus having another structure. In that case, multiple arms are prepared in the X-ray diagnostic apparatus. Then, at least one of the multiple arms is configured to slide along an arc slide axis. Furthermore, an arm that can slide along a slide axis or at least one of the other arms is configured to rotate around a rotation axis by a rotation shaft. Then, the imaging system 6 including the X-ray generating part 11 and the X-ray detector 12 is attached to a slidable arm or at least one of the other arms among the multiple arms. Moreover, a control system that performs imaging of an object O by controlling the multiple arms and the imaging systems 6 is installed in the X-ray diagnostic apparatus.

Then, the imaging function by the interlocking operational mode and the independent operational mode can be installed in an X-ray diagnostic apparatus by configuring the control system so as to control the multiple arms and the imaging system 6 with switching the first mode, in which each of the multiple arms independently starts to move and stops, and the second mode, in which the multiple arms simultaneously start to move at the time of a movement start of the imaging system 6 while the multiple arms simultaneously stop at the time of a stop of the imaging system 6.

What is claimed is:

1. An X-ray diagnostic apparatus comprising:
a first arm rotating around a first rotating axis and sliding along a first arc-like rail relatively to the first rotating axis;
a second arm rotating around a second rotating axis and sliding along a second arc-like rail relatively to the second rotating axis;
a holding structure connected with a first arm side and configured to hold the second arm;
an X-ray tube and an X-ray detector installed on the second arm; and
a control circuit configured to control the first arm and the second arm with switching a first mode and a second mode, each of the first arm and the second arm being independently started to move and stopped relative to each other in the first mode, the first arm and the second arm being moved with interlocking with each other in the second mode.

2. An X-ray diagnostic apparatus of claim 1, wherein at least the first arm is configured to slide along the first rail by a slide guide mechanism having a holding structure in which balls roll on at least one arc-like rail.

3. An X-ray diagnostic apparatus of claim 1, further comprising:
a rotating structure for rotating the second arm around the second rotating axis inclined by a movement of the first arm.

4. An X-ray diagnostic apparatus of claim 1, further comprising:
a bed, for setting an object, which inclines according to an inclined direction of the second rotating axis.

5. An X-ray diagnostic apparatus of claim 3, further comprising:
processing circuitry configured to
generate frames of X-ray image data based on X-ray detection data detected by the X-ray detector during a rotation of the second arm around the inclined second rotating axis, and
generate three dimensional image data based on the frames of the X-ray image data.

6. An X-ray diagnostic apparatus of claim 1, wherein the control circuit is configured to start movements of the first arm and the second arm simultaneously at a movement start time of the X-ray tube and the X-ray detector and stop the first arm and the second arm simultaneously at a stop time of the X-ray tube and the X-ray detector, by controlling moving speeds of the first arm and the second arm respectively.

7. An X-ray diagnostic apparatus of claim 6, wherein the control circuit is configured to
move the first arm and the second arm in a first moving speed mode in a first moving range until the first arm and the second arm lie predetermined positions respectively, and
move the first arm and the second arm in a second moving speed mode in a second moving range after the first arm and the second arm lie the predetermined positions respectively, the second moving speed mode having higher speeds than speeds in the first moving speed mode.

8. An X-ray diagnostic apparatus of claim 1, wherein the first arm is attached to a ceiling, a wall surface or a floor, using a rotating shaft around the first rotating axis as a support post.

9. An X-ray diagnostic apparatus of claim 1, wherein the first arm slides in a slide range along the first rail and the second arm slides in another slide range along the second rail, the slide range of the first arm being shorter than the slide range of the second arm.

10. An X-ray diagnostic apparatus of claim 2, wherein the slide guide mechanism has a holding structure having balls rolling on each of bearing planes formed on four corners of the rail.

11. An X-ray diagnostic apparatus of claim 2, wherein the slide guide mechanism has a holding structure having circulating balls partially rolling on the at least one arc-like rail.

12. An X-ray diagnostic apparatus comprising:
a first arm sliding along a first arc-like rail and holding an X-ray tube and an X-ray detector;
a holding structure which slidably holds the first arm and slides along a second arc-like rail;

a second arm attached to at least one of a ceiling, a floor and a wall, the second arm slidably holding the holding structure; and a control circuit configured to control the first arm and the second arm with switching a first mode and a second mode, each of the first arm and the second arm being independently started to move and stopped relative to each other in the first mode, the first arm and the second arm being moved with interlocking with each other in the second mode.

* * * * *